United States Patent [19]

Cohen

[11] Patent Number: 5,245,408
[45] Date of Patent: Sep. 14, 1993

[54] ELECTRO-OPTIC COHERENT LIGHT DETECTOR

[75] Inventor: Jonathan D. Cohen, Hanover, Md.

[73] Assignee: The United States of America as represented by the Director, National Security Agency, Washington, D.C.

[21] Appl. No.: 647,624

[22] Filed: Jan. 11, 1991

[51] Int. Cl.⁵ ............................................. G01B 9/02
[52] U.S. Cl. .................................. 356/351; 356/352; 356/353; 356/346; 356/347; 250/338.1
[58] Field of Search ............... 356/351, 352, 353, 359, 356/347, 346; 250/338, 339

[56] References Cited

U.S. PATENT DOCUMENTS

| | | | |
|---|---|---|---|
| 3,824,018 | 7/1974 | Crane | 356/112 |
| 4,217,036 | 8/1980 | Chang | 350/358 |
| 4,309,108 | 1/1982 | Siebert | 356/352 |
| 4,595,292 | 6/1986 | Amodeo | 356/346 |
| 4,600,307 | 1/1986 | Krohm et al. | 356/346 |
| 4,735,507 | 4/1988 | Crane | 356/351 |
| 4,743,114 | 5/1988 | Crane | 356/346 |
| 4,744,658 | 5/1988 | Holly | 356/351 |
| 4,874,223 | 10/1989 | O'Meara | 350/163 |
| 5,076,699 | 12/1991 | Ryan et al. | 356/437 |

OTHER PUBLICATIONS

J. Jannson, T. Jannson, and E. Wolf: "Spatial Coherence Discrimination In Scattering," Optics Letters, vol. 13, 12, Dec. 1988, pp. 1060–1062.
C. J. Duffy and D. Hickman: "A Temporal Coherence-Based Optical Sensor," Sensors and Actuators, vol. 18, 1989, pp. 17–31.

Primary Examiner—Samuel A. Turner
Assistant Examiner—LaCharles P. Keesee
Attorney, Agent, or Firm—John R. Utermohle; Thomas O. Maser

[57] ABSTRACT

An apparatus is described which detects the presence or absence of coherent light and provides an estimate of the coherent light's wavelength. The apparatus employs a common-path "polarization interferometer" in which the two linear polarization paths act as interferometer legs. Electro-optic modulation is used to effect periodic differential path length changes in the interferometer. The apparatus performs synchronous time-integrating detection on the light emerging from the interferometer to measure coherent contributions in the presence of obscuring incoherent light.

14 Claims, 8 Drawing Sheets

ELECTRO-OPTIC COHERENT LIGHT DETECTOR

BACKGROUND OF THE INVENTION

1. Field of the Invention

This invention relates to the field of optical devices, and more specifically to the electrical detection and processing of coherent light.

2. Description of the Prior Art

The past decade and a half have seen the proposal of many approaches to the detection of coherent light in the presence of incoherent light. Some of these approaches have also rendered additional information about the detected source. To perform detection and other analysis in the presence of high levels of incoherent radiation, the detector must reject constant and fluctuating contributions due to incoherent light. Detection based upon both spatial and temporal coherence has been advocated.

Spatial coherence approaches have been suggested by J. Jannson, T. Jannson, and E. Wolf: "Spatial Coherence Discrimination In Scattering," *Optics Letters*, Vol. 13, No. 12, December 1988, pp. 1060–1062 and by U.S. Pat. No. 4,874,223 to O'Meara. The effectiveness of such approaches in detecting minute levels of coherent light obscured in incoherent light has not been demonstrated and does not exploit the large processing gain available to apparatus using time-integrating methods.

Many approaches have applied temporal modulation to the optical disturbance which preferentially operates on the coherent contribution. The signature of this modulation is then sought in detected optical intensity. Of these approaches, several produce modulation signatures which vary substantially with the incoming wavelength, so that searching of the signatures is required, making detection of strongly obscured coherent light impractical. Apparatus of this type is described by C. J. Duffy and D. Hickman: "A Temporal Coherence-Based Optical Sensor," *Sensors and Actuators*, Vol. 18, 1989, pp 17–31 and disclosed in U.S. Pat. Nos. 3,824,018 and 4,743,114 to Crane and U.S. Pat. No. 4,309,108 to Siebert.

The most promising methods for obtaining sensitivity while rejecting incoherent light are those which apply a periodic modulation. These produce intensity fluctuation components whose period is known precisely, allowing nearly arbitrary gain against the random fluctuations due to noise. Crane, in U.S. Pat. No. 4,735,507, discloses several such arrangements which effect the modulation by undesirable mechanical means. Crane's apparatus also permits determination of wavelength but in a manner which does not offer gain against noise and will not function when the coherent light is obscured by incoherent light.

Amodeo et al. in U.S. Pat. No. 4,595,292 and Krohn et al. in U.S. Pat. No. 4,600,307 have advocated the use of modulated Fabry-Perot etalons for modulation. Thick etalons—the form required here—are difficult to maintain in alignment. Amodeo et al. specifies the use of a liquid crystal in the etalon, severely limiting the modulation speed and thereby permitting only the monitoring of slow phenomena. Krohn et al. specifies that the etalon be modulated by the presence of an ultrasonic sound wave. Such a modulation restricts the optical aperture to less than the wavelength of the ultrasonic wave—a very small and undesirable value for practical systems. Neither Amodeo et al. nor Krohn et al. provides wavelength information.

U.S. Pat. No. 4,217,036 to Chang discloses apparatus which achieves modulation by periodic scanning of the pass band of an acoustooptic filter. Chang's apparatus provides a detected signal whose coherent component is impulsive, so that only a small fraction of the desired signal component is in the low harmonics of the periodicity. This results in great inefficiency and an attendant loss in processing gain. Moreover, spurious harmonics of the drive frequency may be produced by variations in the incoherent-light spectrum, even in the absence of coherent light. Chang does not offer a wavelength measurement.

SUMMARY OF THE INVENTION

It is an object of my invention to provide a time-integrating, periodically modulated apparatus to detect the presence of coherent light which overcomes the limitations of the prior art.

It is a further object of my invention to provide a detector which rejects incoherent light.

It is a still further object of my invention to provide a detector which is simple, stable, and easily constructed.

It is another object of my invention to provide an apparatus which is suitable for monitoring swiftly changing phenomena.

It is still another object of my invention to provide a detector which estimates coherent light wavelength in the possible presence of incoherent light.

An apparatus having these and other desirable features would include input light to be studied, said light emanating from a light source; a modulation signal source which produces a periodic electrical modulation signal; a polarization interferometer, said interferometer comprising an optical polarizer, an optical analyzer, and birefringent modulation means positioned between said polarizer and said analyzer, said birefringent modulation means possessing an optical propagation axis x and two mutually orthogonal axes y and z orthogonal to x, said birefringent modulation means having a first optical path length along axis x for light propagating in the x direction with polarization parallel to the y axis and a second optical path length along axis x for light propagating in the x direction with polarization parallel to the z axis, said first path length differing from said second path length by more than the coherence length of incoherent light, said first path length differing from said second path length by an amount which varies in accordance with said modulation signal; collecting means positioned to receive said input light and direct it through said interferometer; optical detection means which produces an electrical detection signal; focusing means positioned to receive light from said interferometer and direct it to said detection means; and processing means which receives said detection signal, said processing means detecting components of said detection signal which are synchronous with said modulation signal.

BRIEF DESCRIPTION OF THE DRAWINGS

My invention may best be understood when reading the following specification with reference to the drawings, in which.

DESCRIPTION OF THE PREFERRED EMBODIMENTS

Figure 1:
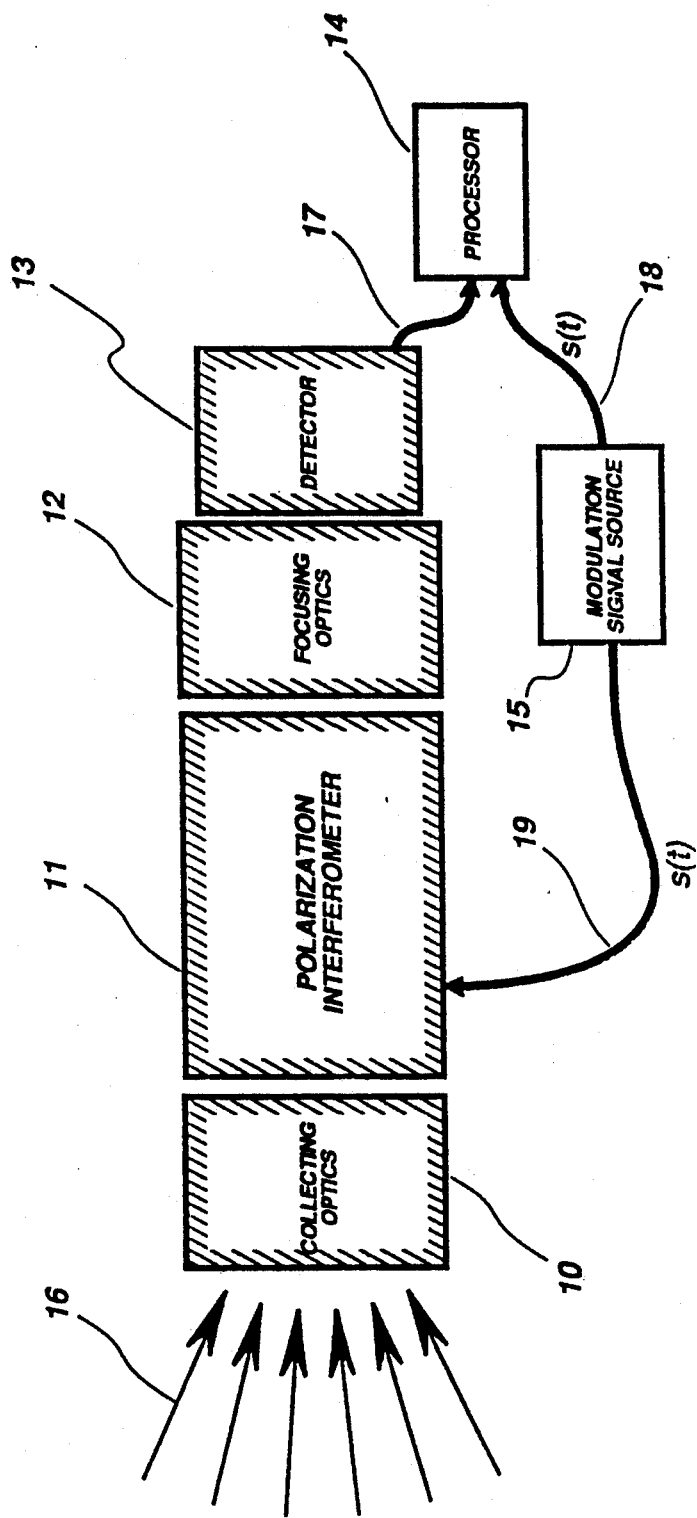
FIG. 1 is a generalized block diagram of my invention.

FIG. 1 illustrates my invention in its most general form. It consists of collecting optics 10, a polarization interferometer 11, focusing optics 12, detector 13, processor 14, and modulation signal source 15. Together, the collecting optics 10 and focusing optics 12 serve to image the field of observation onto the detector 13 in such a way that the light of interest 16 passes through the polarization interferometer 11 and onto detector 13. Division of collecting and focusing optics into assemblies before and after the interferometer is done to best accomplish this goal for the specific application. It should be understood that for some applications, the entire operation of collecting the light, directing it through the interferometer, and imaging the light onto the detector may be accomplished by either the collection optics or the focusing optics. Hence, each of the collecting optics and the focusing optics may consist of any combination of mirrors, lenses, and optical fibers or either may be omitted.

The polarization interferometer 11 is driven by a modulation signal s(t), supplied by modulation signal source 15 via a line 19. The signal s(t) causes modulation of the interferometer's optical properties, as described hereinbelow. The electrical output signal generated by the detector 13 is provided via line 17 to processor 14, which recognizes the presence or absence of the desired optical input.

Figure 2:
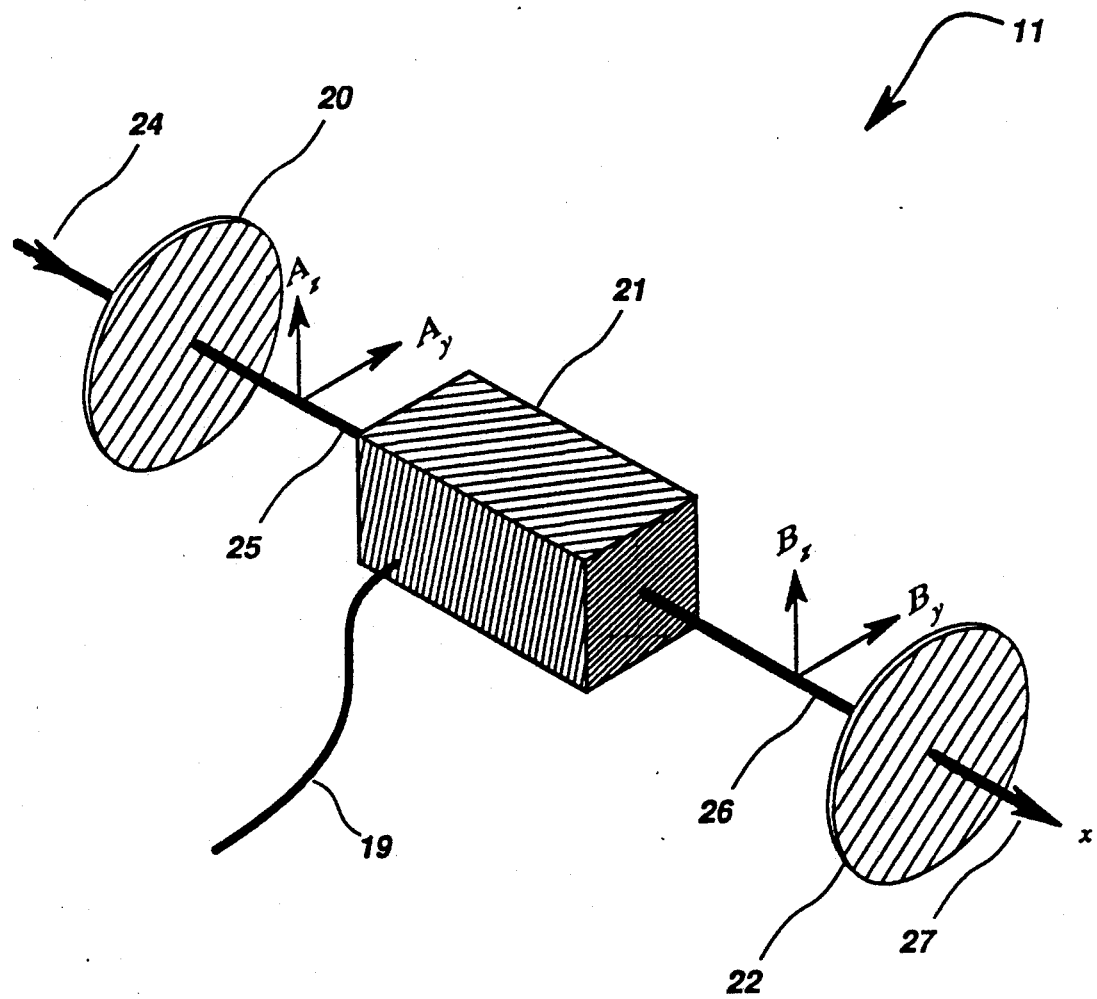
FIG. 2 is a exploded view of the general polarization interferometer of FIG. 1.

The general polarization interferometer is illustrated in FIG. 2. The purpose of the interferometer is to apply amplitude modulation to temporally coherent light, while effecting no amplitude modulation on incoherent light. It consists of polarizer 20, birefringent modulator 21, and analyzer 22. The orientation and purpose of these devices is described in detail below. Like much of the apparatus in the prior art, the interferometer imposes a path length difference which exceeds the coherence length of the incoherent light but not that of the coherent light. Unlike most prior art approaches, however, my invention applies modulation whose form is precisely known.

The interferometer 11 will be described as it operates on a single light ray 24 passing through it, though in a practical application it will operate on more complex and realistic optical disturbances in a similar manner. It should also be understood that while my invention is described herein in terms of light, it is capable of operating on radiation throughout the electromagnetic spectrum and this disclosure should be viewed in this more general context.

A light ray 24 entering the interferometer is incident on polarizer 20 which passes only the component having linear polarization in the direction 45 degrees to both the y and z axes. See FIG. 2 for the definition of these components. Let the incident light have temporal stationary coherence function $\Gamma(\tau)$, where $\tau$ is time difference. In this description, the spatial variation is suppressed, as this analysis is carried out on a ray of light.

Light 25 leaving polarizer 20 may be resolved into its two components having time-varying complex magnitudes $A_y(t)$ and $A_z(t)$, the linear polarizations parallel to the y and z axes, respectively. These two magnitudes are equal and their mutual coherence function is $$\left\langle A_y(t)A_z^*(t+\tau) = \tfrac{1}{2}\Gamma(\tau), \right\rangle$$

where the asterisk indicates complex conjugation.

The two polarizations then pass through birefringent modulator 21. Birefringent modulator 21 is aligned with its principal axes parallel with the y and z axes so that each polarization passes through the modulator unrotated and emerges in the same polarization. Light 26 leaving the modulator has polarization components $B_y(t)$ and $B_z(t)$, respectively. A modulation signal s(t) is presented to the modulator by way of line 19. The modulator imposes a different effective path length for each polarization. In particular, $$B_y(t) = A_y\left(t - \frac{a_y + b_y s(t)}{c}\right)$$

and $$B_z(t) = A_z\left(t - \frac{a_z + b_z s(t)}{c}\right),$$

where s(t) is the modulation signal described above, c is the speed of light, and the constants $a_y$, $a_z$, $b_y$, and $b_z$ depend upon the size and optical properties of the modulator. (Practical examples of these constants are given below.) Thus, the mutual coherence function of the two polarizations is $$\left\langle B_y(t)B_z^*(t+\tau) \right\rangle = \tfrac{1}{2}\Gamma\left(\frac{a_y - a_z + (b_y - b_z)s(t)}{c} + \tau\right).$$

Light leaving the birefringent modulator encounters analyzer 22 oriented 45 degrees to both the y and z axes. This analyzer produces linearly polarized light whose amplitude is the sum of equal contributions from the two impinging polarizations, reduced by a factor of $\sqrt{2}$. Thus, the light 27 leaving the analyzer has intensity $$I(t) = \tfrac{1}{2}\left\langle |B_y(t) + B_z(t)|^2 \right\rangle =$$

$$\tfrac{1}{2}\left[\Gamma(0) + \mathrm{Re}\,\Gamma\left(\frac{a_y - a_z + (b_y - b_z)s(t)}{c}\right)\right].$$

Now let the modulator be described by the more convenient parameters $$a = a_y - a_z$$

and $$b = b_y - b_z.$$

Then $$I(t) = \frac{1}{2}\left[\Gamma(0) + Re\Gamma\left(\frac{a + bs(t)}{c}\right)\right].$$

The detector 13 responds in proportion to this intensity.

From the above discussion, one may see that an interferometer is formed by polararizer 20 acting as a beam splitter, analyzer 22 acting as a beam combiner, and birefringent modulator 21 providing two optical paths, one for each polarization.

Let V denote the maximum absolute value of signal s(t). In order to reject incoherent light of coherence length l, the values of a and b are chosen so that $$|a| - |b|V > l.$$

With this choice, the intensity for incoherent light is $$I(t) = \tfrac{1}{2}\Gamma(0).\text{ (incoherent light)}$$

Conversely, when light of much longer coherence length L is present, say of wavelength λ, then $$I(t) = \frac{1}{2}\Gamma(0)\left[1 + \cos\left(2\pi\frac{a + bs(t)}{\lambda}\right)\right], \text{ (coherent light)}$$

provided that $$|a| + |b|V < L.$$

In practice, $$|a| > |b|V$$

so that the condition for obtaining the stated responses to incoherent and coherent light is $$L > |a| > l.$$

With this condition satisfied, coherent light may be recognized by the time varying behavior of the intensity. Accordingly, processor 14 operating on the detected signal received over line 17 is designed to look for the time-varying behavior described above. Incoherent light, which does not produce such time variation, is largely ignored.

Consider the case of coherent illumination with wavelength λ and sinusoidal modulation signal $$s(t) = V\cos(2\pi ft).$$

Although it is understood that other forms of s(t) may be used in my invention, a sinusoid is the prefered choice. In this case, the intensity consists of terms oscillating at frequencies which are multiples of the excitation frequency f. These terms are weighted by Bessel functions whose arguments depend upon b and λ:

$$I(t) = \frac{1}{2}\Gamma(0)\left[1 + \cos\left(\frac{a}{\lambda}\right)J_0\left(\frac{Vb}{\lambda}\right) + \right.$$

$$2\cos\left(\frac{a}{\lambda}\right)\sum_{k=1}^{\infty}(-1)^k J_{2k}\left(\frac{Vb}{\lambda}\right)\cos(2\pi(2k)ft) -$$

$$\left. 2\sin\left(\frac{a}{\lambda}\right)\sum_{k=0}^{\infty}(-1)^k J_{2k+1}\left(\frac{Vb}{\lambda}\right)\cos(2\pi(2k+1)ft)\right],$$

where the functions $\{J_k\}$ are the Bessel functions of the first kind. In particular, the first four harmonics of the drive frequency have magnitudes $$h_1 = \Gamma(0)\left|\sin\left(\frac{a}{\lambda}\right)J_1\left(\frac{Vb}{\lambda}\right)\right|,$$

$$h_2 = \Gamma(0)\left|\cos\left(\frac{a}{\lambda}\right)J_2\left(\frac{Vb}{\lambda}\right)\right|,$$

$$h_3 = \Gamma(0)\left|\sin\left(\frac{a}{\lambda}\right)J_3\left(\frac{Vb}{\lambda}\right)\right|,$$

and $$h_4 = \Gamma(0)\left|\cos\left(\frac{a}{\lambda}\right)J_4\left(\frac{Vb}{\lambda}\right)\right|,$$

respectively.

The processor 14 is designed to measure $h_1$ and $h_2$ to detect the presence of coherent radiation. In addition, $h_3$ and $h_4$ may be measured to obtain an approximation of the wavelength of radiation.

Figure 3:
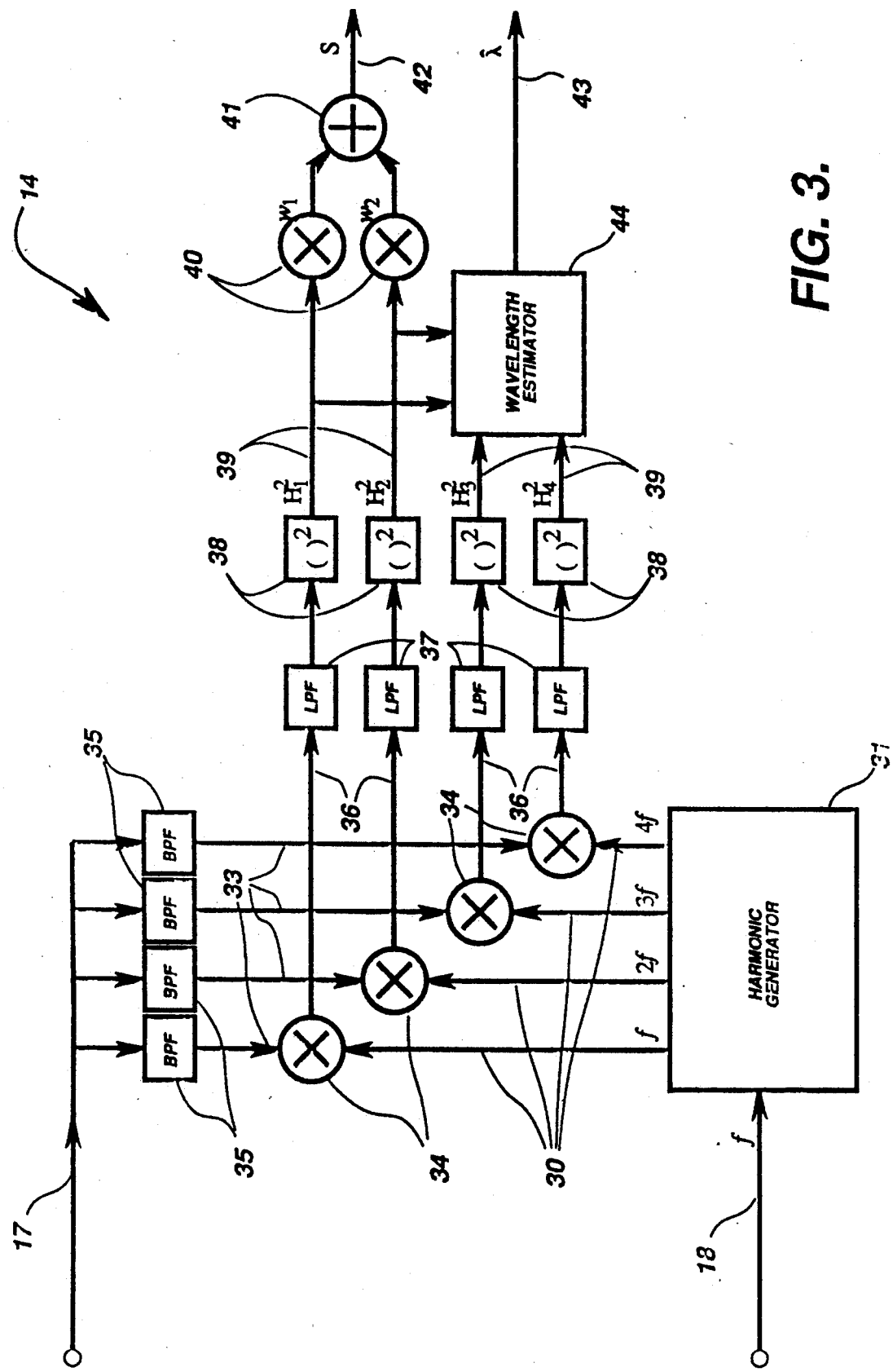
FIG. 3 illustrates an embodiment of the processor of FIG. 1.

A block diagram of one embodiment of processor 14 to be used with sinusoidal modulation is illustrated in FIG. 3. The modulation signal s(t), provided to polarization interferometer 11 over line 19, is also provided to processor 14 via line 18. Processor 14 uses this signal as a reference for detecting the modulation in the detected signal 17. Harmonics of the reference s(t) are generated by a harmonic generator 31 for each term to be measured and these are used to downconvert the detected signal to baseband. The nth harmonic of s(t) is a tone at frequency nf. The detected signal arriving via line 17 is routed through a plurality of bandpass filters 35-35 to provide a group of signals filtered about the desired harmonics of s(t): the signal to be downconverted by the nth harmonic of s(t) is a bandpass filtered about the frequency nf. This rejects much of the noise which would otherwise overload the mixers 34-34. Each harmonic of s(t) is routed over one of the lines 30-30 to one of the mixers 34-34, where it is mixed with its corresponding filtered detected signal on one of the lines 33-33. The phases of the tones on lines 30-30 are adjusted by generator 31 to insure they are appropriate to compensate for phase changes throughout the rest of the electrical and optical system.

The downconverted signals on lines 36-36 are filtered through low pass filters 37-37 of cutoff frequency B. This cutoff frequency is small to obtain good rejection of noise. The signal power exiting each low pass filter, produced by squarers 38-38, is measured, producing on lines 39-39 an estimate, $(H_i)^2$ of $(h_i)^2$, where i is 1, 2, 3, or 4, depending upon whether the first, second, third, or fourth harmonic of the reference was used for down-conversion, respectively.

The estimates $(H_1)^2$ and $(H_2)^2$ are weighted by multipliers 40-40 and summed by summer 41 to produce on line 42 a statistic, $$S = w_1 H_1^2 + w_2 H_2^2 = \Gamma^2(0)F(\lambda) + \text{(noise terms)},$$

where $$F(\lambda) = R^2 \Re^2(\lambda) \left[ w_1 \sin^2\left(\frac{a}{\lambda}\right) J_1^2\left(\frac{Vb}{\lambda}\right) + w_2 \cos^2\left(\frac{a}{\lambda}\right) J_2^2\left(\frac{Vb}{\lambda}\right) \right],$$

and where $\Re(\lambda)$ is the detector responsivity, R is the detector load resistance, and $w_1$ and $w_2$ are constants set to make $F(\lambda)$ be as near to unity as possible over the wavelengths of interest. The statistic S has a mean which increases with the coherent light power and may be used to determine whether or not coherent light is present and to provide a crude estimate of the light's power.

Denote the set of wavelengths of interest by $\Lambda$. To overcome noise, the product Vb is chosen so that $J_1(Vb/\lambda)$ and $J_2(vb/\lambda)$ have apreciable values for all $\lambda \epsilon \Lambda$. In practice, a is large number compared with the optical wavelengths, and the sine and cosine in the function F cause the major contribution to oscillate between $h_1$ and $h_2$ as the wavelength is varied. To see how to pick $w_1$ and $w_2$, define the extrema $$m_i = \min_{\lambda \epsilon \Lambda}\left\{ R\Re(\lambda)J_i\left(\frac{Vb}{\lambda}\right) \right\}$$

and $$M_i = \max_{\lambda \epsilon \Lambda}\left\{ R\Re(\lambda)J_i\left(\frac{Vb}{\lambda}\right) \right\},$$

for $i = 1, 2$. To minimize the maximum possible multiplicative error, one chooses $$w_i = \frac{1}{m_i M_i}.$$

Then the maximum possible multiplicative error (neglecting noise) is a factor of $$\max\left\{ \frac{M_1}{m_1}, \frac{M_2}{m_2} \right\}.$$

As an example, let $\Lambda$ be the interval of 0.55 to 0.82 micron. Then a choice of vb=2 microns results in $Vb/\lambda\epsilon[2,3]$, with $0.33 < J_1(Vb/\lambda) < 0.58$ and $0.35 < J_2(Vb/\lambda) < 0.49$. With a flat responsivity, the maximum error of measuring the light power is about $\pm 2.4$ dB.

The values of $(H_3)^2$ and $(H_4)^2$ may be used to determine the wavelength by comparing them to $(H_1)^2$ and $(H_2)^2$, for in the absence of noise, $$R_1 = \frac{H_3^2}{H_1^2} = \frac{J_3^2\left(\frac{Vb}{\lambda}\right)}{J_1^2\left(\frac{Vb}{\lambda}\right)}$$

and $$R_2 = \frac{H_4^2}{H_2^2} = \frac{J_4^2\left(\frac{Vb}{\lambda}\right)}{J_2^2\left(\frac{Vb}{\lambda}\right)}.$$

Either of these ratios may be used to determine $\lambda$, provided that Vb and $\Lambda$ are such that unique values are obtained. To avoid numerical instability, one chooses the first or second ratio, depending upon whether $(H_1)^2$ or $(H_2)^2$ is larger, respectively. The operation of computing $R_1$ and $R_2$ and using these values to determine an estimate 43 of $\lambda$ is carried out by wavelength estimator 44.

For the numerical example above, both $R_1$ and $R_2$ are monotonic in $\lambda$, ensuring unique determination of $\lambda$ in $\Lambda$. In fact, over this range, $R_1$ and $R_2$ are nearly exponential in $Vb/\lambda$, covering a range of about 12 dB for $R_1$ and 9 dB for $R_2$.

Note that the value of b may vary somewhat with wavelength, causing small modifications to the described behavior, and perhaps requiring some modification to the interpretation of results.

The processing apparatus pictured in FIG. 3 need not be implemented in analog hardware. Indeed, the squaring operation, performed on very low bandwidth signals, would be realized in digital hardware much more easily. Moreover, a system which attempts to obtain extreme sensitivity would require large dynamic range in the mixers—a requirement met more practically in the digital domain. In general, the preferred approach is to implement at least a portion of the processing in digital hardware, perhaps using software, and perhaps to the point of digitizing immediately and implementing the entire processing operation digitally.

Now consider the details of the birefringent modulator 21. Several embodiments of this portion of the apparatus shall be discussed here, illustrated in FIGS. 4, 5, 6 and 8, in which the entire birefringent modulator is shown.

Figure 4:
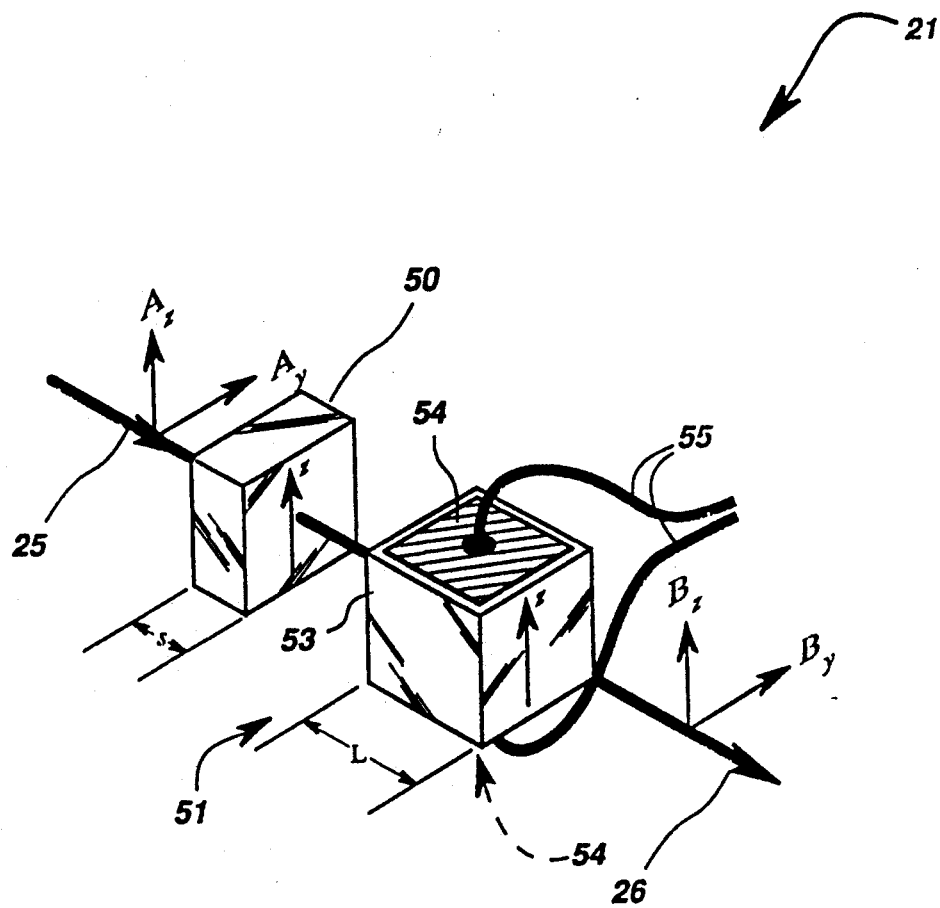
FIG. 4 illustrates an embodiment of the birefringent modulator of FIG. 2 using a nonbirefringent electro-optic modulator.

According to the embodiment illustrated in FIG. 4, birefringent modulator 21 includes a fixed retarder 50 and an electro-optic modulator 51 arranged along an axis such that a ray of light 25 will pass through them serially. Electro-optic modulator 51 possesses no birefringence in the absence of an applied voltage. Electro-optic modulator 51 and retarder 50 both have their optic (z) axes perpendicular to the direction of optical propagation.

Retarder 50 serves to introduce the constant path delay identified as $a$ in the above analysis. This delay arises from the difference between the ordinary index $n_o$ experienced by light of the y polarization and the extraordinary index $n_e$ experienced by light of z polarization. After passing through the retarder of length s, the difference in path lengths between the two polarizations is $$a = s(n_o - n_e)$$

Electro-optic modulator 51 consists of a block of electro-optic material 53 fitted with parallel plates 54-54 perpendicular to the z axis. Wires 55-55 attached to the plates allow the modulation voltage to be applied. The material 53 possess no quiescent birefringence, but when an electric field is applied via the plates, a birefringence is induced which is proportional to the field strength E. In particular, if the material is cubic having symmetry 43 m, then the change in index in the z polarization is $$\Delta n_z(t) = -\frac{r_{41}n^3}{2} E(t),$$

where n is the quiescent index and $r_{41}$ is the electro-optic coefficient. Similarly, the change in the y-polarization index is $$\Delta n_y(t) = \frac{r_{41}n^3}{2} E(t).$$

Now, let H be the height (z extent) of the electro-optic material block and L be the length (x extent). With the voltage s(t) applied to the modulator, the path length difference imposed by the modulator is $$L(\Delta n_y(t) - \Delta n_z(t)) = Lr_{41}n^3 E(t) = Lr_{41}n^3 \frac{s(t)}{H},$$

so that the quantity b used in the analysis above is given by the product of a material constant and a geometric factor:

$$b = (r_{41}n^3)\left(\frac{L}{H}\right).$$

As an example of this type of birefringent modulator, consider the use of GaP as an electro-optic material 53 and quartz as the retarder 50. At visible red wavelengths, GaP has the figure of merit $r_{41}n^3 = 35$ pm/V. Thus, to achieve the Vb of 2 microns suggested earlier, one would require $$V\left(\frac{L}{H}\right) = 4.9 \times 10^4 \text{ volts.}$$

In quartz, $n_o = 1.54$ and $n_e = 1.55$ in the red. Thus, $a = -0.01s$, and a 100 micron decorrelating distance could be achieved with a retarder of 1 cm thickness. (The indices do change with wavelength, an effect which would not be significant here.)

The polarization interferometer described here is similar to some standard electro-optic modulators, with the exception that a small path delay (but much longer than optical wavelengths) has been deliberately introduced by inclusion of retarder 50.

Figure 5:
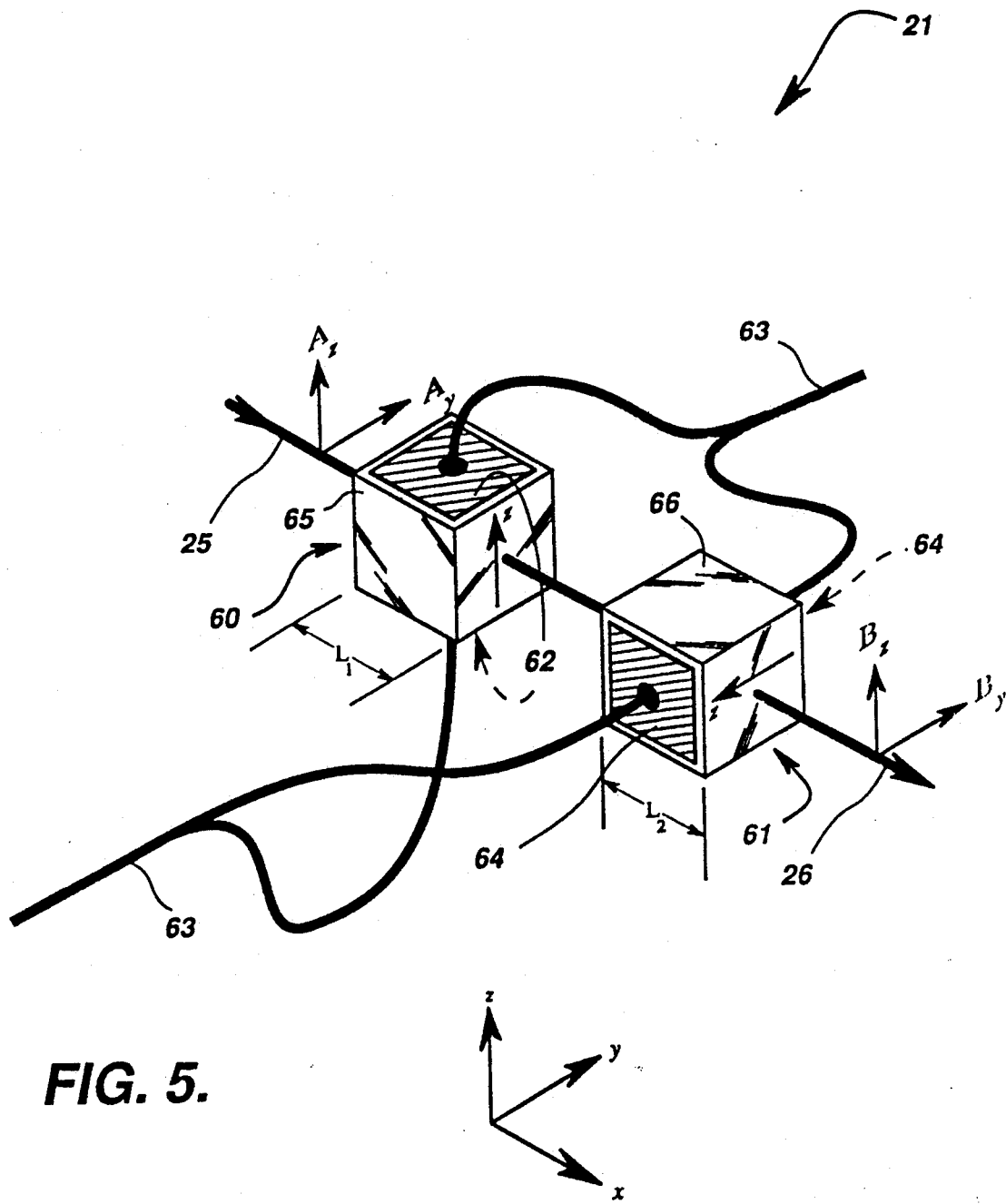
FIG. 5 illustrates an embodiment of the birefringent modulator of FIG. 2 using two birefringent electro-optic modulators.
Figure 6:
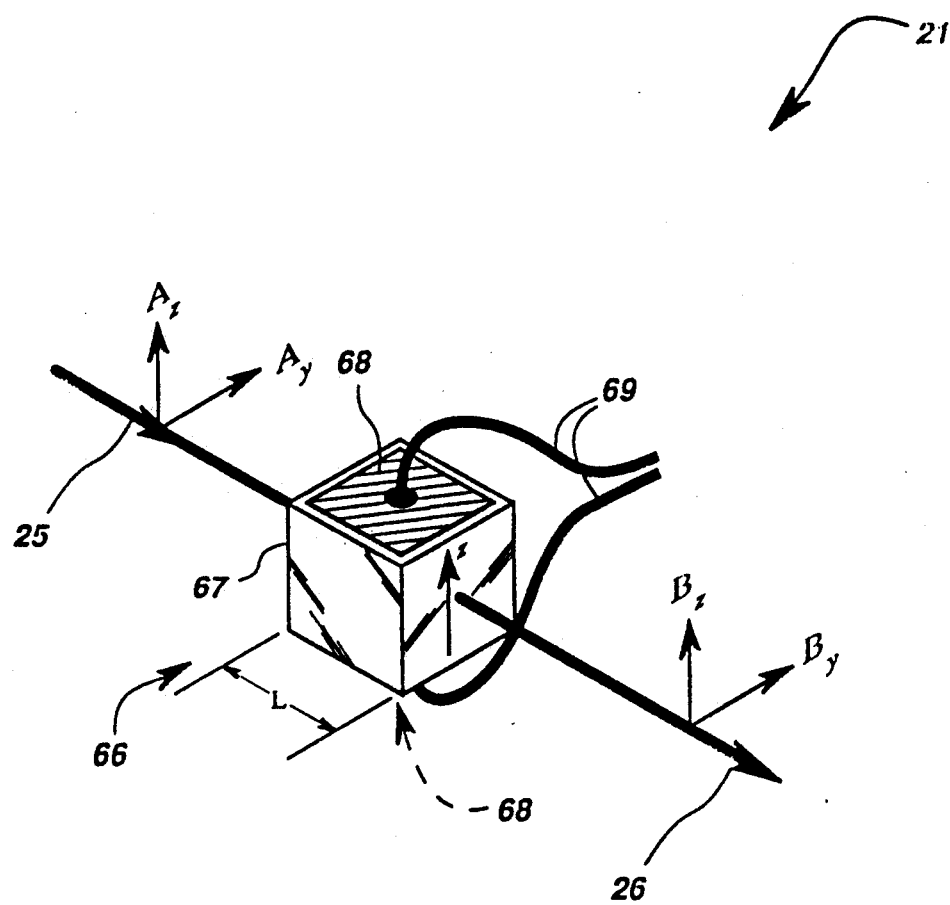
FIG. 6 illustrates an embodiment of the birefringent modulator of FIG. 2 using one birefringent electro-optic modulator.
Figure 6:
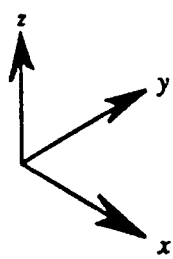

According to the embodiment illustrated in FIG. 5, birefringent modulator 21 includes a first electro-optic modulator 60 and a second electro-optic modulator 61, arranged along an axis such that a ray of light 25 will pass through them serially. Modulator 60 is constructed of a block of electro-optic material 65 fitted with parallel plates 62-62 perpendicular to the crystalline z axis of material 65. Modulator 61 is constructed of a block of electro-optic material 66 fitted with parallel plates 64-64 perpendicular to the crystalline z axis of material 66. The electro-optic material in block 65 of this embodiment is the same as the material in block 66. This material differs, however, from the material in block 53 of modulator 51 of the previous embodiment. The difference is that block 65 and 66 of this embodiment each exhibit birefringence even in the absence of applied field resulting from a voltage on lines 63-63.

Light passes serially through the two blocks perpendicular to their z axes. The blocks 65 and 66 are oriented such that the two crystalline z axes are perpendicular, so that the portion of light 25 polarized parallel to the optic axis in the first block is polarized perpendicular to the optic axis in the second block. The first block 65 is of length $L_1$, while the second block 66 is $L_2$ long. In the absence of applied voltage, then, the path difference experienced by light of the two polarizations passing through the combination is $$a = L_1 n_o + L_2 n_e - (L_1 n_e + L_2 n_o)$$
$$= (L_1 - L_2)(n_o - n_e)$$

The difference in length is chosen to effect the desired decorrelation length.

The plates 62-62 of modulator 60 and plates 64-64 of modulator 61 are connected in parallel by wires 63-63, but with opposing polarity. Wires 63-63 are used to apply the modulation signal. Combined with the orthogonal orientation, this connection causes the induced index changes to reinforce.

The structure illustrated in FIG. 5 is similar to electro-optic modulators which have been constructed for temperature compensated modulation. The difference here is that $L_1$ is deliberately made different from $L_2$.

Consider the use of a material with 3m symmetry with field E applied along the optic (z) axis as described. Then the y and z polarizations experience the induced index changes $$\Delta n_y = -\tfrac{1}{2} r_{13} n_o^3 E$$

and $$\Delta n_z = -\tfrac{1}{2} r_{33} n_e^3 E,$$

where $r_{33}$ and $r_{13}$ are electro-optic coefficients. With a crystal height of H, the difference in path length induced by the applied voltage s(t) is $$bs(t) = \frac{1}{2} \frac{L_1 + L_2}{H} (r_{33} n_e^2 - r_{13} n_o^2) s(t)$$

so that $$b = \frac{1}{2} \frac{L_1 + L_2}{H} (r_{33} n_e^2 - r_{13} n_o^2).$$

As an example, consider LiNbO$_3$ as the electro-optic material for modulators 60 and 61. In the red, $r_{33}n_e^2 - r_{13}n_o^2 = 215$ pm/V and $n_o - n_e = 0.086$. Thus, to achieve Vb=2 microns, one must have $$V \frac{L_1 + L_2}{H} = 18.6 \text{ kV.}$$

In addition, to achieve a decorrelating distance of a=100 microns, one would want $$L_1 - L_2 = 1.1 \text{ millimeters}.$$

This value, of course, is not critical. It is only necessary that the incoherent light be decorrelated, the coherent light of interest remain correlated, and the imaging system be able to tolerate the differences in path length.

It should be understood that while the use of two modulators 60 and 61 is preferred, my invention will function with only one such modulator. Indeed, though using one birefringent electro-optic modulator will result in inferior performance, such an embodiment may be used to reduce complexity and cost. The modified embodiment of the birefringent modulator 21 is pictured in FIG. 6, comprising only birefringent electro-optic modulator 66. Modulator 66, like modulators 60 and 61, is comprised of a block 67 of electro-optic material which is birefringent in the absence of an electric field. Block 67 is fitted with plates 68-68 to apply a field in the direction of the optic axis, via lines 69-69. The birefringent modulator 21 so constructed behaves like the apparatus of FIG. 4, with the quiescent birefringence equivalent to that introduced by retarder 50, and the field-induced birefringence being equivalent to that introduced by electro-optic modulator 51.

Figure 7:
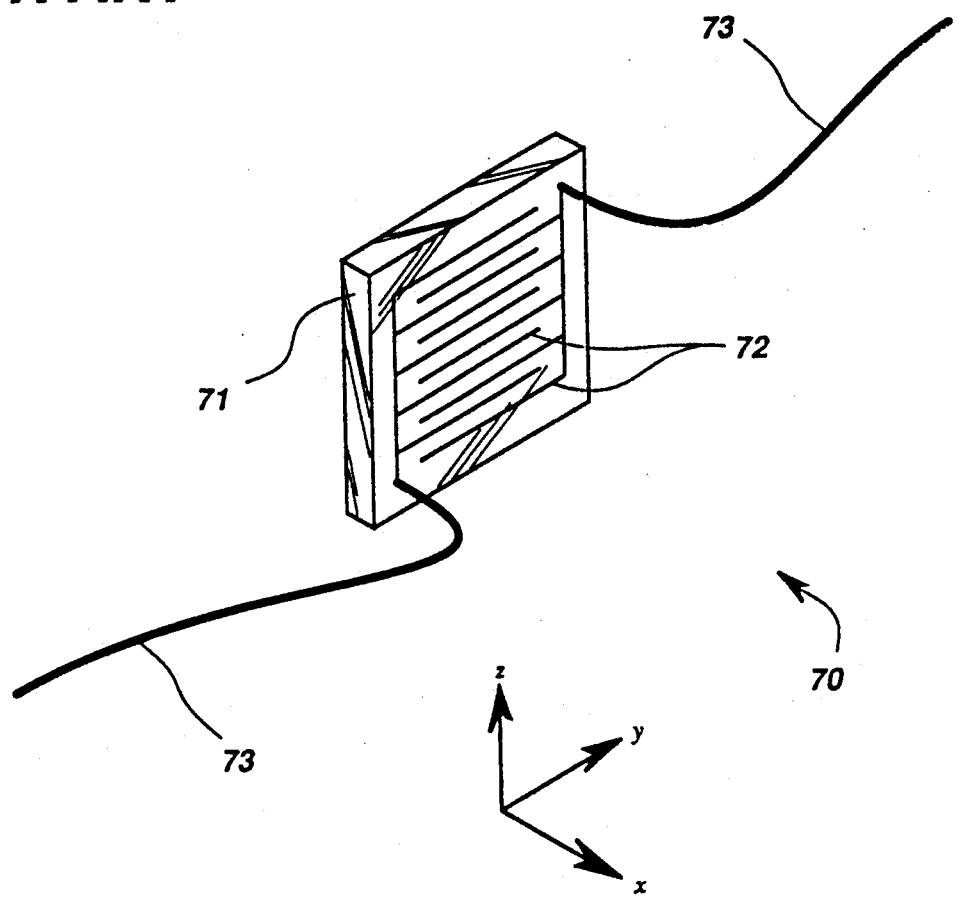
FIG. 7 is an illustration of an electro-optic plate modulator found in the prior art.
Figure 8:
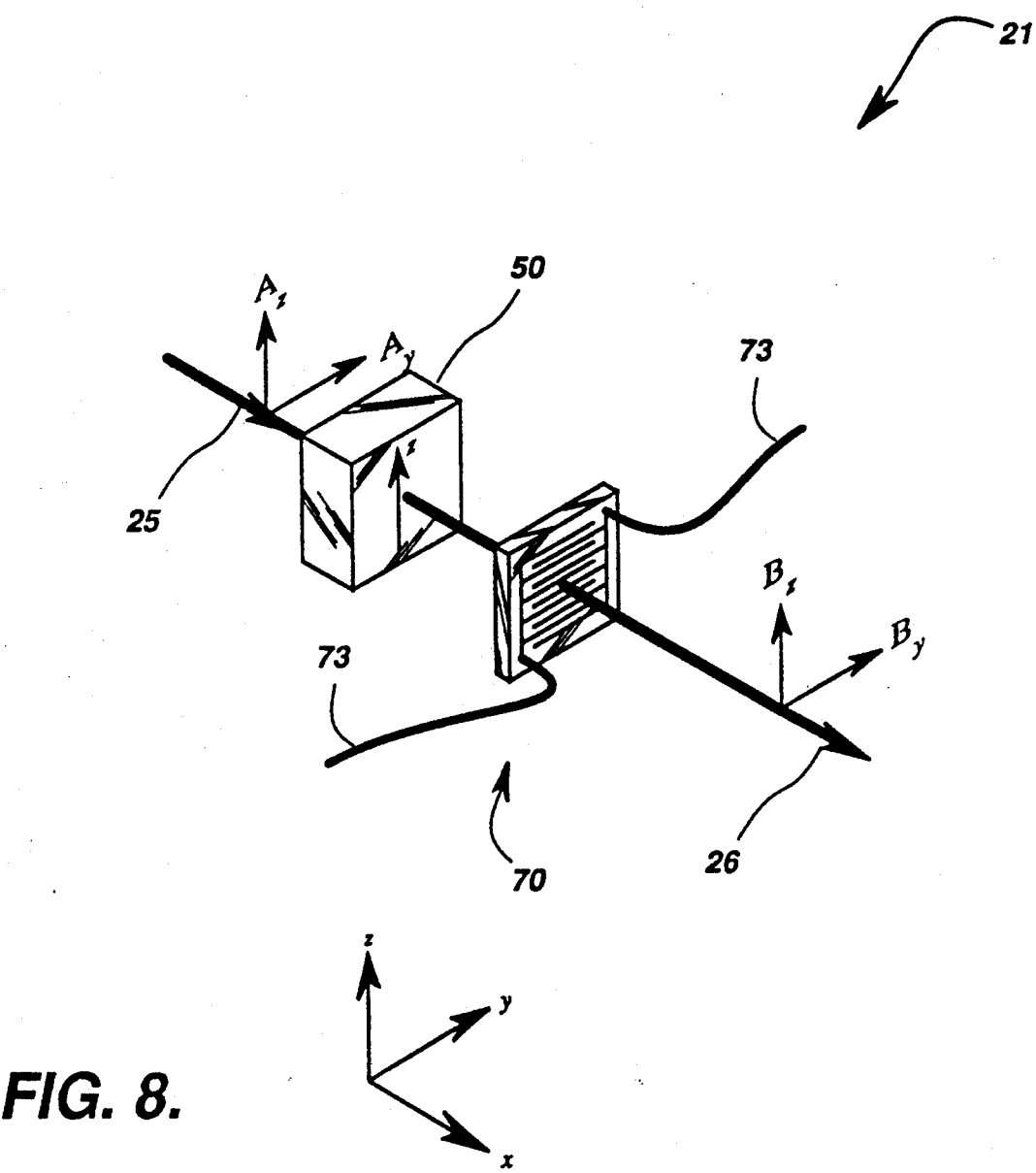
FIG. 8 illustrates an embodiment of the birefringent modulator of FIG. 2 using the electro-optic plate modulator of FIG. 7.

As a alternative to constructing my invention with electro-optic modulators which use rectangular prisms with electrodes on the sides, my invention may be constructed using electro-optic plate modulators, wherein the optical path through the electro-optic material is small compared to the lateral extent of the modulator. Such a device is pictured in FIG. 7. The electro-optic plate modulator 70 is comprised of a thin plate 71 of electro-optic material whose faces are fitted with electrodes 72-72. (In the illustration, only one face is fitted with electrodes, through both sides may, in general, have electrodes.) Wires 73-73 are provided to apply a voltage to the electrodes. The electrodes are interdigitated so that an electric field which is substantially parallel to the optic axis of the material may be introduced by applying a voltage to wires 73-73. Modulators similar to 70 of FIG. 7 may be used in place of modulator 51 of FIG. 4, modulators 60 and 61 of FIG. 5, or modulator 66 of FIG. 6. In particular, FIG. 8 illustrates an embodiment of the birefringent modulator using electro-optic plate modulator 70 in place of electro-optic modulator 51 of FIG. 4. The plate modulator more easily accommodates a large angular aperture.

It should also be understood that my invention may exploit the quadratic electro-optic effect, rather than the above-described linear electro-optic effect, in the electro-optic modulators. The quadratic electro-optic effect produces optical pathlength variations which are proportional to the square of the applied field. If quadratic electro-optic materials are used in place of the linear electro-optic materials, then my invention will behave in a similar fashion, but with the desired optical intensity components being produced on higher harmonics. Thus, when using quadratic electro-optic materials, detection of a coherent light source is accomplished by examining the second and fourth harmonic of the modulation signal. In particular, PLZT may be used as a quadratic electro-optic material to achieve high efficiency with a small pathlength. PLZT is thus well suited for use in a plate modulator, and the preferred embodiment of my invention using PLZT as an electro-optic material uses the birefringent modulator illustrated in FIG. 8.

As one of the primary objects of my invention is to detect coherent light while ignoring the perturbations due to incoherent light, it is necessary to consider the effects of noise arising from detector dark current, Johnson noise, and shot noise.

The following model will be chosen for analysis: The detector is characterized by a sensitive area A, a responsivity $\Re(\lambda)$, which may vary with wavelength, a load resistance R, and a dark electron generation rate of $\lambda_d$. It is operated at absolute temperature T. The detector is illuminated by a thermal (and incoherent) source supplying an average intensity I, and a coherent source whose intensity is sinusoidally modulated (100%) at a frequency of f. The detector's output is then beat down to baseband by multiplication with a sine wave of unit amplitude at frequency f. The result is then passed through an ideal low pass filter of cutoff frequency B. The filter's output is squared and sampled to produce the statistic X. It is also assumed that the coherence time of the incoherent light is much less than the inverse of the low pass filter's bandwidth—a nearly universal situation.

This model holds for estimating each of the harmonic amplitudes.

Using standard analytical techniques known to those skilled in the art, one finds that the output mean is the sum of a "bias" $\mu_b$ (which does not depend on the coherent illumination) and a "signal" $\mu_s$ (which depends only on the coherent illumination). In particular $$\mu_b = (eR)^2 B \left( \lambda_d + \lambda_i + \frac{2kT}{e^2 R} \right)$$

and $$\mu_s = (eR)^2 \left( \frac{\lambda_c^2}{4} + B\lambda_c \right) \approx \left( \frac{eR\lambda_c}{2} \right)^2,$$

where e is the electron charge, k is Boltzmann's constant, $\lambda_i$ is the mean photoelectron generation rate due to the incoherent light, and $\lambda_c$ is the mean photoelectron generation rate due to the coherent light. (The latter contribution to $\mu_s$ is not likely to be significant.) Hence, $$E\{X\} = (eR)^2 B \left( \lambda_d + \lambda_i + \lambda_c + \frac{2kT}{e^2 R} \right) + (eR)^2 \frac{\lambda_c^2}{4}.$$

The output variance, in the absence of the coherent light, is found to be $$Var\{X\} = 2(eR)^4 B^2 \left( \lambda_d + \lambda_i + \frac{2kT}{e^2 R} \right)^2$$

$$= 2\mu_b^2.$$

In terms of the illumination, $$\lambda_i = \frac{IA \Re m}{e}$$

and

-continued $$\lambda_c = \frac{P_c \Re(\lambda)}{2e},$$

where $$m = \int \frac{I(\lambda)}{I} \Re(\lambda) d\lambda$$

is the mean responsivity, $I(\lambda)/I$ is the normalized intensity as a function of wavelength (whose integral is 1), and $\lambda$ is the coherent light wavelength.

To ensure that $\mu_s$ is some s standard deviations above the bias, one requires that $\mu_s > (1+\sqrt{2S})\mu_b$, that is, that $$\lambda_c > 2\sqrt{(1+\sqrt{2}\,s)B\left(\lambda_d + \lambda_i + \frac{2kT}{e^2R}\right)}$$

or $$P_c > \frac{4e}{\Re(\lambda)}\sqrt{(1+\sqrt{2}\,s)B\left(\lambda_d + \frac{IA\Re m}{e} + \frac{2kT}{e^2R}\right)}.$$

The minimum sensitivity (achieving the required number of standard deviations above bias), in the absence of incoherent background radiation, is $$P_c > \frac{4}{\Re(\lambda)}\sqrt{(1+\sqrt{2}\,s)\frac{2kTB}{R}\left(1+\frac{\lambda_d e^2 R}{2kT}\right)}.$$

When the incoherent background is strong enough to dominate the internally generated noise, then the minimum coherent light power is $$P_c > \sqrt{(1+\sqrt{2}\,s)\frac{16BIAe}{\Re(\lambda)}\left(\frac{\Re\,m}{\Re(\lambda)}\right)}.$$

As an example, consider a detector operated at 290° K. with a load resistance of 10kΩ, a dark current swamped by Johnson noise, a responsivity of 0.5 A/W, and an aperture of 1 cm². Suppose that a low pass filter with a cutoff frequency of 1 Hz is chosen, and that one desires the signal to be 10 standard deviations above the bias. Then with no incoherent background, the coherent light must have power $P_c > 28$ pW. Now suppose that the detector receives incoherent illumination of 100 mW/cm². Then the coherent light must have power $P_c > 2.8$ nW, a factor of 100 higher than with no background.

The results above apply to any one of the four estimates calculated in the detector processing. To combine such estimates one observes that each of the four estimates $\{H_i\}$ is independent of the others. (This is a slight approximation: There is a dependence introduced by the "excess noise" of the thermal source. This contribution is too small to be significant.) In particular, then, the means and the variances add when the statistics are summed.

Consider now the detection of coherent light using the statistic S. The system is illuminated by incoherent light of intensity $I_o$ and coherent light of power $P_o$. The coherent light is of wavelength $\lambda$, has a polarization which is at an angle of $\theta$ with respect to the polarizer at the entrance to the interferometer, and is assumed to be collected completely by the detector. The incoherent light is captured by an aperture of size A.

The coherent light powers oscillating at the first and second harmonic of f are $$P_1 = 2P_o\left|\cos^2(\theta)\sin\left(\frac{a}{\lambda}\right)J_1\left(\frac{Vb}{\lambda}\right)\right|$$

and $$P_2 = 2P_o\left|\cos^2(\theta)\cos\left(\frac{a}{\lambda}\right)J_2\left(\frac{Vb}{\lambda}\right)\right|,$$

respectively. With incident incoherent intensity of $I_o$, the detector sees $\frac{1}{4}$ of this light (due to loss at the polarizers), so that $I=I_o/4$.

The bias of S (no signal) is $$\mu_b = (eR)^2 B\left(\lambda_d + \frac{IA\Re m}{4e} + \frac{2kT}{e^2R}\right)(w_1 + w_2)$$

and the signal component of the mean is $$\mu_s = P_o^2 \frac{F(\lambda)\cos^4(\theta)}{4}.$$

The variance is $$Var\{S\} = 2\mu_b^2 \frac{w_1^2 + w_2^2}{(w_1 + w_2)^2}.$$

To ensure that $\mu_s$ is some s standard deviations above the bias, one requires that $$\mu_s > (1 + rs)\mu_b,$$

where $$r = \frac{\sqrt{2(w_1^2 + w_2^2)}}{w_1 + w_2}$$

specifies the unbalance between the weights. In particular, the minimum power detectable (at s standard deviations above bias) with no incoherent background is given by $$[P_o]_{no\ background} = \sqrt{\frac{8(1 + rs)RkTB(w_1 + w_2)}{F(\lambda)}\left(1 + \frac{e^2R\lambda_d}{2kT}\right)}.$$

With a strong incoherent background whose shot noise dominates the internal noise, the minimum coherent power is $$[P_o]_{large\ background} = \sqrt{\frac{(1 + rs)eR^2BIA\,\Re_m(w_1 + w_2)}{F(\lambda)}}.$$

In these equations, it is helpful to note that $F(\lambda) \approx 1$, $r \approx 1$, and $w_1$ and $w_2$ are on the order of $4(R\Re_m)^{-2}$.

As a numerical example, again let Λ be the interval of 0.55 to 0.82 microns with Vb=2 microns so that $0.33 < J_1(Vb/\lambda) < 0.58$ and $0.35 < J_2(Vb/\lambda) < 0.49$. With a flat responsivity, $0.57 < F(\lambda) < 1.74$. Also, r=1.00. Now suppose that the detector is operated at 290° K. with a load resistance of 10 kΩ, a dark current swamped by Johnson noise, a responsivity of 0.5 A/W, and an aperture of 1 cm². Suppose that a low pass filter with a cutoff frequency of 1 Hz is chosen, and that one desires the signal to be 10 standard deviations above the bias. Then with no incoherent background, the coherent light must have a power of 30 to 50 pW, depending on its wavelength. Now suppose that the detector receives incoherent illumination of 100 mW/cm². Then the coherent light must have a power of 1.5 to 2.6 nW.

The numerical examples above assumed a flat responsivity. The inclusion of more realistic responses will not change the order of magnitude of the results.

Except for pathological cases, a coherent source which is modulated will produce nearly the same result as an unmodulated source with equal average power. For general (time varying) coherent power $P_c(t)$, the mean output becomes $$\mu_s(t) = \left(\frac{R\Re(\lambda)}{4}\right)^2 \left(\int_{-\infty}^{\infty} P_c(t_0)h_F(t-t_0)dt_0 + \int_{-\infty}^{\infty} P_c(t_0)[2\cos(2\pi ft_0) + \cos(4\pi ft_0)]h_F(t-t_0)dt_0\right)^2$$

where $h_F(t)$ is the low pass filter's impulse response. The first integral above is just the average coherent power (averaged through the low pass filter). The second integral only contributes if $P_c(t)$ has significant components near the frequencies f or 2f. In particular, if the coherent source pulses at a rate which is not harmonically related to the system's drive frequency, the system will respond as if the source were of constant power over the effective observation time imposed by the low pass filter.

Many variations of the hereinabove embodiments may be made. One may, for example, remote the detector from the interferometer, joining them by an optical fiber bundle which may be incoherent. This would avoid any radio frequency coupling between the modulating field and the detector which might arise.

The detection of tones in the output may be accomplished by superheterodyne receivers, that is, by translating each tone to an intermediate frequency for amplification before detecting its amplitude.

A portion or all of the detection process may be implemented in digital hardware. The detector's output, after amplification, may be digitized directly, along with the modulation source. Alternatively, the modulation may be derived from the digital clock, allowing very simple digital downconversion.

The interferometer may be placed in an imaging system to view the coherent contribution to an entire scene. Since imaging detectors usually sample the scene slowly, a slow modulation must be employed. Downconversion and integration would then be performed on the detected scene by multiplying the detected pixel values by the modulation function before accumulating them in a video memory. Wavelength information could be provided as described above.

The materials and numerical values suggested hereinabove serve only to illustrate my invention's embodiment and power and are not to be considered exclusively. Though the specification hereinabove described my invention in terms of light, it should be understood that my invention is applicable to other areas of the electromagnetic spectrum.

Those skilled in the art will recognize that embodiments may vary substantially from those illustrated herein without deviating from the spirit of my invention. I intend that my invention be limited only by the following claims.

I claim:

1. An electro-optic coherent light detector, comprising:
    (a) means for propagating light along a propagation axis x;
    (b) a periodic electrical modulation signal source;
    (c) a polarization interferometer disposed along said propagation axis x, said interferometer comprising:
        (i) an optical polarizer;
        (ii) an optical analyzer; and
        (iii) a birefringent modulator positioned between said polarizer and said analyzer and responsive to said modulation signal, said birefringent modulator having two mutually orthogonal axes y and z orthogonal to x and having a first optical path along axis x for light propagating in the x direction with polarization parallel to the z axis and a second optical path along axis x for light propagating in the x direction with polarization parallel to the y axis, the difference between the lengths of said first and second paths exceeding the coherence length of incoherent light and varying in accordance with said modulation signal; and
    (d) means for detecting intensity components of light from said interferometer which are synchronous with said modulation signal.

2. The apparatus of claim 1 further comprising means for collecting light and directing it through said interferometer.

3. The apparatus of claim 2 further comprising focusing means for receiving light from said interferometer and directing it to said detection means.

4. The apparatus of claim 3 wherein said detection means further comprises means for generating an electrical detection signal.

5. The apparatus of claim 1 wherein said birefringent modulator further comprises first and second elecro-optic modulators oriented such that their optic axes are mutually perpendicular and perpendicular to the propagation axis, said electro-optic modulators having differing lengths along said propagation axis and comprising a rectangular prism of electro-optic material having means for applying said electric modulation signal to said electro-optic material on opposing sides orthogonal to their respective optic axes.

6. The apparatus of claim 1 wherein said birefringent modulator comprises a birefringent retarder and an electro-optic modulator comprising a rectangular prism of electro-optic material oriented such that its optic axis is perpendicular to its propagation axis and having means for applying said electric modulation signal to said electro-optic material on opposing sides orthogonal to its optic axis.

7. The apparatus of claim 1 wherein said birefringent modulator comprises an electro-optic modulator comprising a rectangular prism of electro-optic material oriented such that its optic axis is perpendicular to its propagation axis and having means for applying said electric modulation signal to said electro-optic material on opposing sides orthogonal to its optic axis.

8. The apparatus of claim 1 wherein said birefringent modulator further comprises first and second electro-optic modulators oriented such that their optic axes are mutually perpendicular and perpendicular to the propagation axis, said electro-optic modulators having differing lengths along said propagation axis and comprising a plate of electro-optic material having means for applying said electric modulation signal to said electro-optic material, said application means comprising a plurality of electrodes affixed to one or both faces of said plate orthogonal to said optic axis and to said propagation axis.

9. The apparatus of claim 1 wherein said birefringent modulator comprises a birefringent retarder and an electro-optic modulator comprising a plate of electro-optic material having means for applying said electric modulation signal to said electro-optic material, said application means comprising a plurality of electrodes affixed to one or both faces of said plate orthogonal to said optic axis and to said propagation axis.

10. The apparatus of claim 1 wherein said birefringent modulator comprises an electro-optic modulator comprising a plate of electro-optic material having means for applying said electric modulation signal to said electro-optic material, said application means comprising a plurality of electrodes affixed to one or both faces of said plate orthogonal to said optic axis and to said propagation axis.

11. The apparatus of claim 1 wherein said modulation signal is a sine wave.

12. An electro-optic coherent light detector, comprising:
(a) means for propagating light along a propagation axis x;
(b) a periodic electrical modulation signal source;
(c) a polarization interferometer disposed along said propagation axis x, said interferometer comprising:
  (i) an optical polarizer;
  (ii) an optical analyzer; and
  (iii) a birefringent modulator positioned between said polarizer and said analyzer and responsive to said modulation signal, said birefringent modulator having two mutually orthogonal axes y and z orthogonal to x and having a first optical path along axis x for light propagating in the x direction with polarization parallel to the z axis and a second optical path along axis x for light propagating in the x direction with polarization parallel to the y axis, the difference between the lengths of said first and second paths exceeding the coherence length of incoherent light and varying in accordance with said modulation signal;
(d) means for collecting light and directing it through said interferometer;
(e) means for detecting intensity components of light from said interferometer which are synchronous with said modulation signal, said detecting means further comprising means for generating an electrical detection signal, said electrical detection signal generation means comprising means for measuring the harmonics of said modulation signal, and
(f) focusing means for receiving light from said interferometer and directing it to said detection means.

13. The apparatus of claim 12 wherein said electrical detection signal generation means further comprises means for estimating the wavelength of said input light from said harmonic measuring means.

14. An electro-optic coherent light detector, comprising:
(a) means for propagating light along a propagation axis x;
(b) a periodic electrical modulation signal source;
(c) a polarization interferometer disposed along said propagation axis x, said interferometer comprising:
  (i) an optical polarizer;
  (ii) an optical analyzer; and
  (iii) a birefringent modulator positioned between said polarizer and said analyzer and responsive to said modulation signal, said birefringent modulator having two mutually orthogonal axes y and z orthogonal to x and having a first optical path along axis x for light propagating in the x direction with polarization parallel to the z axis and a second optical path along axis x for light propagating in the x direction with polarization parallel to the y axis, the difference between the lengths of said first and second paths exceeding the coherence length of incoherent light and varying in accordance with said modulation signal; and
(d) means for detecting intensity components of light from said interferometer which are synchronous with said modulation signal, said detection means comprising a two-dimensional detector array and further comprising means for forming the two-dimensional image of the subject light in the plane of said two-dimensional detector.

* * * * *